(12) United States Patent
Thomson et al.

(10) Patent No.: US 9,253,044 B1
(45) Date of Patent: Feb. 2, 2016

(54) QUANTITATIVE ASSESSMENT OF BIOLOGICAL IMPACT USING OVERLAP METHODS

(71) Applicant: Selventa, Inc., Cambridge, MA (US)

(72) Inventors: Ty Matthew Thomson, Arlington, MA (US); Dmitry Vasilyev, Somerville, MA (US); David Drubin, Cambridge, MA (US); Brian Frushour, Cambridge, MA (US)

(73) Assignee: Selventa, Inc., Cambridge, MA (US)

( * ) Notice: Subject to any disclaimer, the term of this patent is extended or adjusted under 35 U.S.C. 154(b) by 108 days.

(21) Appl. No.: 14/148,193

(22) Filed: Jan. 6, 2014

Related U.S. Application Data (60) Provisional application No. 61/749,021, filed on Jan. 4, 2013.

(51) Int. Cl.
*H04L 12/26* (2006.01)
*H04L 12/24* (2006.01)

(52) U.S. Cl.
CPC ........................... *H04L 41/12* (2013.01)

(58) Field of Classification Search
CPC ...................................................... H04L 43/04
See application file for complete search history.

(56) References Cited

U.S. PATENT DOCUMENTS

| | | | |
|---|---|---|---|
| 8,171,134 B2* | 5/2012 | Chen et al. | 709/224 |
| 2010/0146122 A1* | 6/2010 | Prince et al. | 709/226 |
| 2014/0280899 A1* | 9/2014 | Brewster et al. | 709/224 |

OTHER PUBLICATIONS

"Node-Weighted Prize-Collecting Survivable Network Design Problems"—Ali Vakillian, MIT, Apr. 2013 http://www.mit.edu/~vakilian/publication/Ali_Vakilian_Thesis.pdf.*

\* cited by examiner

*Primary Examiner* — Randy Scott
(74) *Attorney, Agent, or Firm* — David H. Judson (57) ABSTRACT

Scores for particular network models (those having a source node connected to a set of measurable downstream nodes via causal edges) are computed across multiple networks by accounting for an overlap between these models in a manner that reduces cross-network redundancy and increases the specificity of the network models for the network in which they are found. According to another aspect, a meta-network model is created for networks by accounting for the occurrence of network models that are found in multiple networks in a manner that reduces the redundancy across networks and that increases the specificity of the network model score. Preferably, this process provides additional weighting factors for each node in the network model.

2 Claims, 4 Drawing Sheets

QUANTITATIVE ASSESSMENT OF BIOLOGICAL IMPACT USING OVERLAP METHODS

TECHNICAL FIELD

This disclosure relates generally to methods and techniques for characterizing the response of biological networks.

BACKGROUND OF THE RELATED ART

Networks provide a powerful framework for describing complex systems in many different areas, ranging from natural and social sciences to computer and electrical engineering. Their quantitative analysis is based on the concepts and properties studied in the mathematical field of graph theory. Leveraging this knowledge can help address challenging problems that arise in concrete situations.

Signed graphs are used in a variety of disciplines including systems biology, where a signed edge relating two nodes may represent the positive or negative regulatory relationship between two biological entities within a network. Recent advances in experimental and computational techniques have enabled systems-wide measurement of biological entities such as gene expressions or protein activities, and facilitated their integration into larger and larger networks. In this context, the derivation of systems-level properties integrating the levels of the individual biological entities with the corresponding graph structure has become of high interest, because it allows relating molecular mechanisms to overall system behavior.

The exposure of organisms to biologically active substances leads to complex responses, with the interplay between DNA, RNA, proteins, and other biological molecules coalescing to define the cellular phenotypes. Investigation of the resulting biological impact to yield coherent mechanistic insights requires methodologies that can leverage molecular profiling technologies that measure systems-wide changes in thousands of molecular species from a single experiment (e.g., transcriptomics, proteomics, or metabolomics).

A variety of approaches that partially address these investigational requirements have been developed. For example, to derive insight into individual mechanisms, transcriptomic data describing the differential gene expressions produced in response to an exposure can be interpreted in light of pre-defined sets of genes with similar functions or expression patterns (as defined by external databases, for example, MSigDB). Methods like Gene Set Enrichment Analysis (GSEA) or Reverse Causal Reasoning (RCR), which are based on the enrichment of these sets within the differentially expressed genes, enable qualitative investigation of experimental data in light of the statistical enrichment of mechanisms represented by each gene set, while other methods like Network Perturbation Amplitude (NPA) scoring provide quantitative assessment of the degree of perturbation of the mechanisms. It should be noted that the RCR and NPA approaches rely on gene sets that are causally downstream of each mechanism, and thus they allow identification (RCR) and quantitation (NPA) of mechanisms that are likely causes of the measured differential gene expression rather than their consequences (e.g., as assumed when activated pathways are identified based on the differential expressions of the transcripts corresponding to their constituting proteins). To gain systems-level mechanistic insights, findings for active molecular mechanisms can be linked to potential systems-level and phenotypic effects using biological networks comprised of relationships between molecules and processes. Such biological networks are available in variety of public and commercial databases (e.g. Kyoto Encyclopedia of Genes and Genomes (KEGG) Pathways). However, formal methods to integrate individual mechanistic findings and network-level relationships are required to assess the global biological impact of an active substance in a mechanistically coherent manner. They can be guided by the NPA approach that contains a first step in this direction, because it combines the individual mechanisms interconnected within a biological network into a single aggregated entity for which the degree of perturbation can be evaluated.

The ability to gain quantitative systems-level mechanistic insight into the effects of exposure to biologically active substances or other environmental insults (together referred to as "exposures") on biological networks using molecular profiling data has a variety of practical applications, from drug development to consumer safety. For example, candidate compounds can be screened for their ability to affect signaling in therapeutically-relevant pathways (e.g., inhibition of cell cycle), or the molecular mechanisms modulated by chemical exposure can be quantitatively evaluated for their possible association with health risk (e.g., induction of DNA damage). Both of these examples highlight the pressing need to assess the biological impact of exposure, whether the ultimate goal is therapeutic intervention or harm reduction. Recently, there has been an increased focus in systems toxicology on systems-oriented methodologies that emphasize understanding the biological impact of chemical exposures with increased mechanistic granularity. In particular, a recent report by the US National Research Council Committee on Toxicity Testing and Assessment of Environmental Agents advocates for a shift away from toxicological assessment at the level of apical endpoints and towards deriving systems-level understanding of the effects of an exposure on the affected toxicity pathways. In this context, approaches that can leverage network-level information together with quantitative assessments of mechanistic effects provide a powerful opportunity to offer true systems-level insights into the biological impact of an exposure.

Although the biological processes mentioned above are highly interconnected, the underlying biological mechanisms can be organized into distinct network models with defined boundaries in order to explicitly capture the cellular signaling pathways in each process. This segmentation enables the independent evaluation of each process that contributes to a distinct function within the cell. The signaling events within a network can be captured as causal relationships representing signed and directed cause-effect relationships (edges) between biological entities, processes, or even other networks (nodes). Because proteins and interactions are often involved in regulating multiple responses, nodes and edges can be shared among multiple networks, providing an explicit representation of the interactions between subnetworks.

Individual nodes within a network may represent entities or activities that can be experimentally measured, and together these measurements can provide insight into the overall function of the network. In addition to individually looking at measurements for individual nodes in the network, it can be advantageous to summarize these measurements into an overall "score" representing the net activation of the network. Furthermore, while it may not be possible to easily measure some of the nodes in a network, it may be possible to obtain a score for some of these nodes that have an associated signature of measurements. A score for one node can similarly combined with scores or measurements for other nodes in the network to provide an overall score for the activation of the network.

BRIEF SUMMARY

A "HYP" is a particular type of network where one "source" node is connected to a set of measurable downstream nodes via causal edges. Typically, a HYP is a specific type of network model comprised of a set of causal relationships connecting a node representing a particular biological activity (e.g., the increase in abundance of activation of a particular kinase, or a more complex network model describing a growth factor signaling pathway) to measurable downstream entities (e.g., gene expression values) that it positively or negatively regulates. According to one aspect of this disclosure, scores for HYPS are computed across multiple networks by accounting for an overlap between these HYPs in a manner that reduces cross-network redundancy and increases the specificity of the HYPs for the network in which they are found. Preferably, this process provides weights for each gene in each HYP across all the networks.

According to another aspect of this disclosure, a meta-HYP is created for networks by accounting for the occurrence of HYPS that are found in multiple networks in a manner that reduces the redundancy across networks and that increases the specificity of the network meta-HYPs. Preferably, this process provides additional weighting factors for each node in the network meta-HYP.

These approaches may take advantage of known HYP or meta-HYP scoring processes that are referenced herein.

The foregoing has outlined some of the more pertinent features of the subject matter of this disclosure. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the disclosed subject matter and the advantages thereof, reference is now made to the following descriptions taken in conjunction with the accompanying drawings, in which.

DETAILED DESCRIPTION

As used herein, the following terms have the following definitions:

A "knowledge base" is a directed network, preferably of experimentally-observed casual relationships among biological entities and processes;

A "node" is a measurable entity or process;

A "measurement node" is a measured entity or process;

A "reference node" represents a potential perturbation to a node;

A "signature" is a collection of measurable node entities and their expected directions of change with respect to a reference node;

A "differential data set" is a data set that has data associated with a first condition, and data associated with a second condition distinct from the first condition;

A "fold change" is a number describing how much a quantity changes going from an initial to a final value, and is specifically computed by dividing the final value by the initial value;

A "signed graph" (i.e., a graph with a signed edge) is a representational structure that, in the context of this disclosure, provides information concerning regulation and signaling in systems biology; in a signed graph, positive directed edges "→" capture activating relationships between two entities (e.g., protein activities), and negative directed edges "⊣" capture inhibitory relationships;

As used herein, a "causally consistent network" is a balanced graph, and a "causally inconsistent network" is an unbalanced graph. As a functional definition, and for a causally consistent network, all paths between any given pair of nodes have the same net sign; for a causally inconsistent network, for any two nodes there exists at least one path with a positive net sign as well as at least one path with a negative net sign. The net sign is positive if there is an even number of "inhibits" or "decreases" edges along the path, and the net sign is negative if there are an odd number of "inhibits" or "decreases" edges along the path.

A "network model" is an interconnected hierarchy, with a top level network organized into subnetworks, wherein signaling events within each subnetwork are captured as causal relationships representing signed and directed cause-effect relationships (edges) between biological entities (nodes) typically based on experimental evidence reported in primary literature. Because proteins and interactions are often involved in regulating multiple responses, many nodes and edges are shared among multiple subnetworks, thus providing an explicit representation of the interaction between subnetworks. At the base of the network model hierarchy are nodes that describe individual molecular mechanisms and that, within a given knowledgebase, may be causally upstream of gene sets representing increased or decreased gene expressions that have been observed upon direct experimental perturbation of the node. These nodes together with their downstream gene expression relationships are called HYPs.

A "HYP" is a particular type of network where one "source" node is connected to a set of measurable downstream nodes via causal edges. Typically, a HYP is a specific type of network model comprised of a set of causal relationships connecting a node representing a particular biological activity (e.g., the increase in abundance of activation of a particular kinase, or a more complex network model describing a growth factor signaling pathway) to measurable downstream entities (e.g., gene expression values) that it positively or negatively regulates.

The networks, subnetworks and HYPs define a priori the range of biological responses that can be assessed within a given experiment.

Network Perturbation Amplitude (NPA) is a known method for assessing the degree of exposure-induced perturbations in biological entities from transcriptomic data. NPA scoring uses the relationships within a HYP to produce a score representing the change in abundance or activity of the corresponding individual or aggregated entity based on the magnitude and direction of changes of the downstream nodes in the HYP. The NPA method can be extended to produce scores for the changes in activity networks.

In particular, the methodology takes as inputs the differential measurements (for example, differential gene expression measurements) obtained for a set of contrasts (e.g., treated vs. control comparisons) to be evaluated and a network model that provides a coherent a priori description of a possible response captured in the experiment. The methodology then integrates the differential measurements with the network model to produce a score for each contrast.

Thus, NPA scoring typically consists in summing the contributions of each node of the network, adjusted by their relative signs with respect to the rest of the nodes in the network, as determined by the edges of the graph. Such an approach is used when the network is causally consistent (or "balanced" in the graph-theoretical language).

The techniques described herein may use NPA scoring, or other types of scoring methods.

Figure 1:
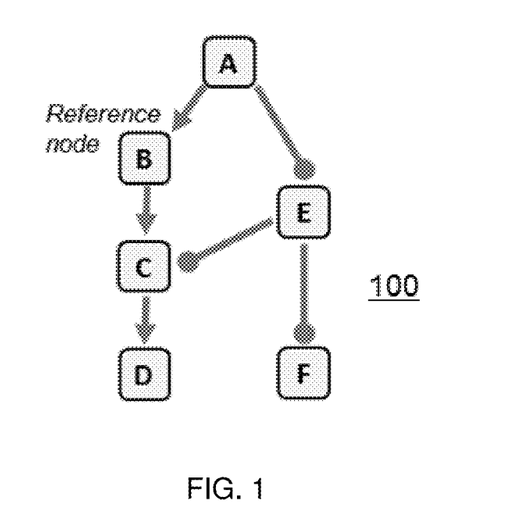
FIG. 1 illustrates a network composed of casual connections between nodes that represent biological entities, processes or other networks.

FIG. 1 represents a network 100 that is composed of causal connections between nodes (A, B, C, D, E, and F) that represent biological entities, processes or other networks. In this network 100, the arrows represent causal increase relationships (e.g., node A increases node B, node B increases node C, and node C increases node D). The edges terminating in a circle represent causal decrease relationships (e.g., node A decreases node E, and node E decreases nodes C and F).

FIG. 1A illustrates a distinct network from that shown in FIG. 1 but that also includes the common node E.

FIG. 1(b) illustrates another network. This network differs from network 100 in FIG. 1(a) but includes one common node, namely, node E.

Figure 2:
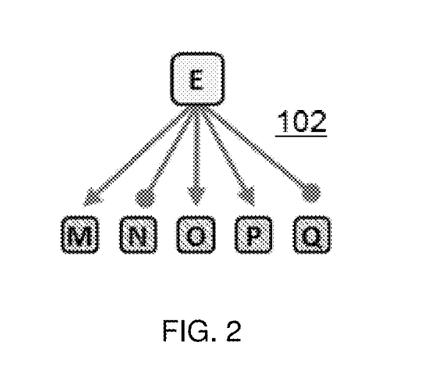
FIG. 2 illustrates a HYP, which is a particular type of network where one source node is connected to a set of measurable downstream nodes via causal edges.

FIG. 2 illustrates a HYP 102. As noted above, a HYP 102 is a particular type of network where one "source" node (here node E) is connected to a set of measurable downstream nodes (here nodes M, N O, P and Q) via causal edges. The measurable nodes are denoted by the diagonal hash coloring.

Figure 3:
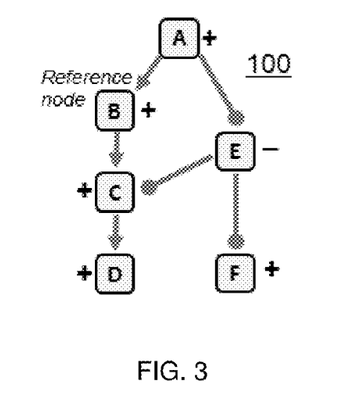
FIG. 3 illustrates the same network as shown in FIG. 1, with each individual node annotated with a sign indicating a net positive or negative causal relationship with a reference node in the network.

FIG. 3 illustrates the same network 100 depicted in FIG. 1, but each node is annotated with a "+" or "−" sign indicating a net positive or negative causal relationship with the reference node (here, node B) based whether that node is connected to the reference node via an even ("+") or odd ("−") number of causal connections via any path connecting those nodes.

Figure 4:
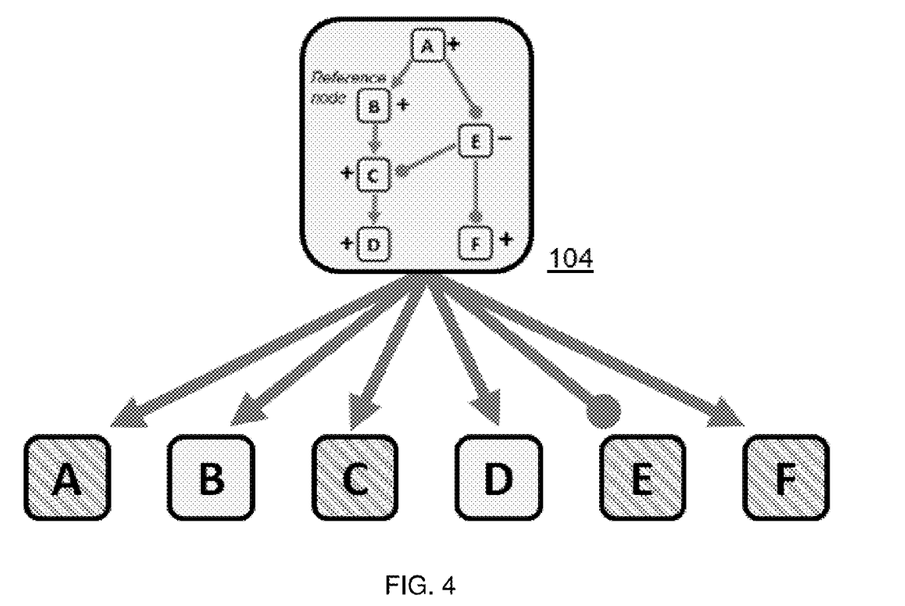
FIG. 4 illustrates the network in FIG. 3 converted into a HYP-like structure, referred to herein as a "meta-HYP"

FIG. 4 illustrates the network from FIG. 3 after it has been converted into a HYP-like structure, which is referred to herein as a "meta-HYP" 104. The meta-HYP is created by connecting a node representing the entire network to each node in the network with a causal increases or causal decreases depending on whether that node has a net positive or negative relationship (respectively) with the reference node. The measurable nodes in the meta-HYP are denoted by the diagonal hash coloring.

Figure 5:
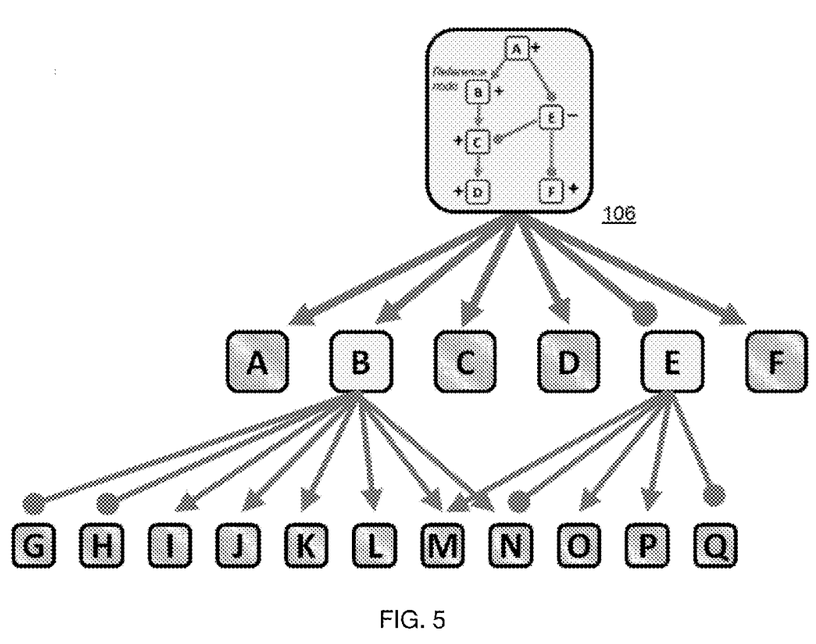
FIG. 5 illustrates a meta-HYP structure according to this disclosure.

FIG. 5 illustrates a meta-HYP 106 where some of the nodes are not measurable but are instead represented by HYPs (nodes B and E in this example) that, in turn, have measurable downstream nodes (e.g., nodes G through Q). The measurable nodes are denoted by the diagonal hash coloring. Note that the HYP for node B and the HYP for node E both share the measurable downstream nodes M and N.

Figure 6:
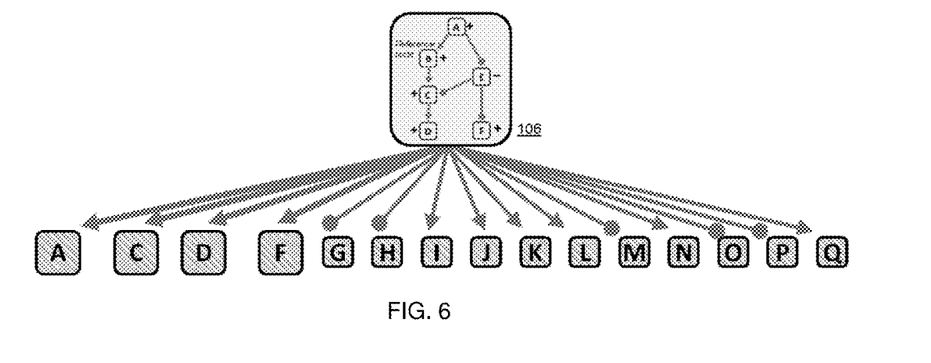
FIG. 6 illustrates the meta-HYP from FIG. 5 converted into a HYP structure according to this disclosure.

FIG. 6 illustrates the meta-HYP 106 from FIG. 5 after it has been converted into a HYP with all of the measurable entities from the meta-HYP and the downstream HYPs combined into a single set of HYP downstream measurable entities. Preferably, each measurable is assigned a weighting factor (not shown) during the HYP construction process.

Figure 7:
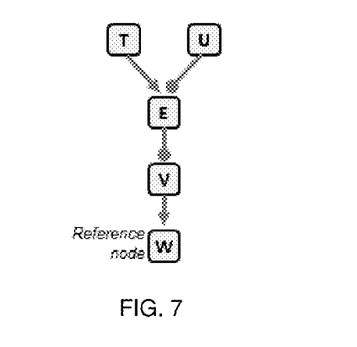
FIG. 7 illustrates a distinct network from that shown in FIG. 1 but that also includes a common node E.

FIG. 7 illustrates a distinct network from that shown in FIG. 1 but that also includes the common node E.

Increasing the Specificity of HYPs Based on their Network Context

Network models can be constructed to describe different biological processes occurring in the same cell, or in different cells. However, often biological molecules are involved in multiple processes, and thus nodes in one network may also appear as nodes in a different network. Generally, HYPs are scored using the full set of downstream measurable nodes, and thus the HYP score is not dependent on the biological network in which that HYP is found. Here, we describe a suite of methods for increasing the specificity of a HYP score based on its context within a network.

The first such method for increasing the specificity of a HYP score is to consider the experimental context in which the relationship between the HYP source node and each downstream measurable node was discovered. To make the HYP more specific for the biological context of a particular network, those downstream nodes in the HYP that were identified from experiments whose context is inconsistent with the context of the biological network can be removed from the HYP before scoring. For example, downstream nodes in a HYP for Tumor Necrosis Factor (TNF) that were identified using HeLa cells, and immortalized cancer cell line, may not be relevant for producing a TNF score specific to a network that describes inflammatory signaling in healthy epithelial cells, and thus could be removed from the HYP prior to scoring. Similarly, to make the HYP more specific for the biological context of a particular network, those downstream nodes in the HYP that were identified from experiments whose context is similar to the context of the biological network can preferentially be included in the HYP for scoring. Similarly, to make the HYP more specific for the biological context of a particular network, those downstream nodes in the HYP that were identified from experiments whose context is similar to the context of the biological network can preferentially be included in the HYP for scoring. For example, downstream nodes in a HYP for TNF that were identified from an experiment using normal human bronchial epithelial cells are likely relevant for signaling in the network that describes inflammatory signaling in healthy epithelial cells, and thus could be left in the HYP for scoring. This method is called Network Context Filtering (NCF).

A similar such method is to only use downstream measurables in a HYP that are known to be associated with the process described by the network, regardless of the experimental context in which the downstream measurable was added to the HYP. For example, gene sets from the Broad Institute's Molecular Signatures Database (MSigDB) relating to epithelial cells or inflammatory signaling could be used to identify genes that are potentially relevant for a network describing inflammatory signaling in epithelial cells, and downstream measurables not present in these gene sets could be removed from HYPs in this network. When using gene sets to filter the HYP downstream nodes, the approach is called Gene Set Filtering (GSF). This approach assumes that downstream nodes that are associated with an independently-determined gene set are more relevant than the downstream nodes that are not associated with the gene set.

Other approaches for improving the specificity of HYP scores rely on the context provided by the other HYPs within the network. These approaches assume that downstream measurable(s) that are found in many HYPs in the network are more likely to be specific to that network than downstream measurable(s) that are found in a small number of HYPs in the network. One implementation of this idea is to remove from HYPs in a network the downstream measurables that are found in less than some minimum percentage of the HYPs in that network (for example, found in less than 30% of the HYPs in that network). This is called the Percent Support (PS) method. Generally, it involves computing a fractional support as a fraction of nodes in the network in which the measurable also contributes, setting to zero the weights for measurables whose fractional support is less than some configurable minimum, and further normalizing the remaining measurable weights for that node to sum to 1, e.g., by dividing all weights by the sum of all remaining weights.

When multiple networks are being considered, the relative context of the set of networks can also guide the selection of downstream measurables that are used to score the HYPs in each network. One implementation of this idea is the Highest Support (HS) method. In particular, for each downstream measurable that is found in HYPs in multiple networks, identify which network has the highest fraction of its HYPs containing that downstream measurable, and then only using that measurable in the scoring of HYPs in that network. In this approach, for a given measurable the fractional support for each network is computed as the fraction of HYPs in each network in which that measurable contributes. The measurable weight is then set to zero in all HYPs in all networks except the network in which the measurable has the highest fractional support. After this process has been carried out for all measurables, the measurable weights are normalized to sum to 1 for each HYP in each network by dividing all weights by the sum of all remaining weights in that HYP.

Whereas the Highest Support method only allows each downstream measurable to contribute to HYP scores in the network that offers the most support for that measurable (as judged by the fraction of HYPs that contain that measurable), a Downweight Promiscuous Measurables (DPM) method weights the contribution of each measurable to the scores for HYPs in each network based on the number of HYPs in that network in which is it found. Specifically, this approach involves counting the number of HYPs in each network that contain each measurable. Let $M_{ij}$ be the number of HYPs in network j that contain measurable i. The weighting factors associated with each measurable in each HYP in network j are then adjusted by the fraction of HYPs across all networks containing that measurable that are in network j (i.e., $M_{ij}/\Sigma_l M_{il}$). For example, consider a HYP in network j whose score is computed using the strength algorithm:

$$\text{Strength}_j = \sum_i W_i d_i \beta_i$$

where $\beta_i$ is the log-fold-change of the measurement for node i, $d_i \in \{-1, +1\}$ is a direction associated with the predicted regulation (increase or decrease) of node i in the meta-HYP, and $W_i$ is the weighting factor associated with node i (generally, $W_i=1/N$, where N is the number of measurables in the HYP, although other methods may produce different weights $W_i$). The Downweight Promiscuous Measurable method would produce new weights $W_i'$ according to:

$$W_i' = \frac{f_{ij} W_i}{\sum_k f_{kj} W_k}, f_{ij} = M_{ij} / \sum_l M_{il}$$

Thus, in the DPM approach, for each measurable used to compute a node score, a promiscuity weight is computed as the number of nodes in that network in which that measurable also contributes, divided by the number of nodes in which that measurable contributes across all networks (including that network). A new weight for that measurable for that node is then computed by multiplying the original measurable weight by the promiscuity weight, and once this process has been carried out for all measurables in a HYP, the measurable weights for that HYP are re-normalized to sum to 1 by dividing each measurable weight by the sum of all measurable weights in that HYP.

Increasing the Specificity of Networks

The scores for HYPs in a network can be amalgamated into a network score as described in Ser. No. 61/746,728, filed Dec. 28, 2012. Briefly, this process involves transforming a network into a meta-HYP (a HYP where at least some of the downstream entities are other HYPs instead of measurable; as shown in FIGS. 3-4. This meta-HYP can then be scored using HYP scoring methods, for example, the Strength method (as described in PCT/US2011/038703), or the GPI method (as described in PCT/EP/2012/061035), where the scores for the downstream HYPs are considered in place of measurements as described in Ser. No. 61/746,728, filed Dec. 28, 2012. Furthermore, additional methods may be used to transform the meta-HYP into a HYP by replacing each HYP with its set of measurable downstreams and weighting the downstreams appropriately (see, FIGS. 5-6). The network score can likewise be computed from this network-derived HYP.

Because two or more networks may share common nodes and HYPs, and furthermore because different HYPs in different networks may share common downstream measurable, network scores may not be entirely specific for signaling in that particular network and may instead reflect the signaling in other networks with shared HYPs and/or downstream measurable. According to a further aspect of this disclosure, a set of additional methods for increasing the specificity of network scores is provided, as is now described.

When considering a set of networks, HYPs that appear in multiple networks are less informative and less indicative of the activation of any particular network. Thus, a Downweight Promiscuous HYP (DPH) method is provided for weighting HYPs within meta-HYPs based on the number of networks in which they appear. Specifically, the contribution of each HYP k to a network score is weighted by $1/N_k$, where $N_k$ is the number of networks under consideration that contain HYP k. For example, consider computing a network score by applying the strength formula to the meta-HYP $$\text{Strength} = \sum_k W_k d_k \beta_k$$

where $\beta_k$ is the score for downstream HYP k or the log-fold-change of the measurement for node k, $d_k \in \{-1, +1\}$ is a direction associated with the predicted regulation (increase or decrease) of node k in the meta-HYP, and $W_k$ is the weighting factor associated with node k. The Downweight Promiscuous HYP method would produce new weights $W_k'$ according to:

$$W'_k = \frac{W_k/N_k}{\sum_l W_l/N_l}$$

The new weights $W_k'$ can be used to compute the network score directly, or be used as weights during the process of collapsing the meta-HYP into a HYP, as described in Ser. No. 61/746,728, filed Dec. 28, 2012.

Thus, given a tree graph comprising a root node, and a set of child nodes, the DPH method involves computing a new node weight for each child node by dividing the weight associated with each child node by the number of other networks in the set of networks that also contain that child node, and further normalizing the new node weights to sum to 1 by dividing all new node weights by the sum of all new node weights.

Another method for increasing the specificity of network scores is called the Correlation Minimization (CM) method, which is now described. This method acts directly on the network HYPs that are produced from meta-HYPs (see FIG. 6). In this approach, and for each network, a weight vector is constructed with an entry for each measurable that is in any of the network HYPs under consideration. The weight vector contains the weights $W_k$ for each measurable in the network HYP, and it contains zeros for measurable that are not in that network HYP but appear in the network HYPs for other networks under consideration. The Correlation Minimization (CM) method attempts to make the network scores more specific by increasing the independence of the network HYPs by increasing the independence of the weight vectors. In one embodiment, a cosine similarity is computed for the weight vectors for each pair of networks under consideration. The pair of networks with the highest absolute value of the cosine similarity is identified, and the measurable that has the largest contribution to the cosine similarity (largest product of weights for that measurable in the two HYPs multiplied by the sign of the cosine similarity) is removed from all network HYPs. This can be accomplished by setting the value for that measurable to zero in all weight vectors, or removing the entry altogether from all weight vectors. Alternatively, instead of removing the measurable with the largest contribution to cosine similarity, the top 3 or 5 (or any other number, or fixed percentage) contributors to the cosine similarity can be identified, and the one present in the fewest number of network HYPs (fewest number of non-zero values in the weight vectors) can be removed. This variation biases the process to increase the independence of network scores while trying to minimize the side effects across all networks. As an alternative, the Pearson correlation coefficient can be used in place of the cosine similarity.

The following section provides additional background.

Accounting for HYP Overlaps

Many HYPs may be supported by overlapping sets of measurements (see, FIG. 5), leading to interdependences between their scores, a decreased ability of these scores to capture the biology specifically perturbed in these HYPs, and ultimately interfering with our ability to derive specific mechanistic insights. To reduce the effects of such overlaps, as described in Ser. No. 61/746,728, filed Dec. 28, 2012, the meta-HYP scoring process may be modified to adjust the contribution $w_i$ of each HYP i to the meta-HYP score based on how much that HYP overlaps with other HYPs in the meta-HYP. This process provided the highest weight to unique HYPs, and lower weights to HYPs that were similar to other HYPs.

As described in Ser. No. 61/746,728, to quantify how much overlap exists between downstream HYPs in a meta-HYP, the expected correlation between HYP scores may be calculated as follows. Consider two HYPs (two constant vectors) $e_1$ and $e_2$ with N downstream measurements (values are 0 for measurables not in the HYP, −1 for measurables connected by a causal decrease relationship, and +1 for measurables connected by a causal increase relationship), and a differential measurement vector X for the measurements in the HYPs (a random vector with N independent components, not necessarily Gaussians, having the same standard deviation σ). The cosine between the vectors $e_1$ and $e_2$ provides a measure of the similarity of the measurements supporting these HYPs. Furthermore, for the Strength scoring method, it is straightforward to show that the cosine between $e_1$ and $e_2$ is the expected correlation between the scores for these two HYPs for any set of measurements:

$$S_1 = e_1^T X, \; S_2 = e_2^T X$$

$$\mathrm{corr}(S_1, S_2) = \frac{e_1^T e_2}{\|e_1\| \|e_2\|} = \cos(e_1, e_2).$$

In one embodiment, the overlap weights $w_i$ are then calculated using expected correlation matrix, using an inverse absolute row-sums of the corresponding rows. In general, the larger the absolute row-sum, the more corresponding subnetwork is correlated with the others. Specifically, the overlap weights may be computed as:

$$w_i = \frac{1 \Big/ \sum_j |\cos(e_i, e_j)|}{\sum_i \left(1 \Big/ \sum_j |\cos(e_i, e_j)|\right)}$$

Thus, in the above approach, given a tree graph comprising a root node, and a set of child nodes, HYP overlaps may be accounted for by computing a cosine similarity of each pair of scored child nodes, where the cosine similarity is the cosine between vectors of the weights for each measurable used to compute each child node score (and wherein a measurable not used to compute the score for any child node preferably has a measurable weight of zero). A new node weight for each child node is then computed by dividing the original node weight by the sum of the cosines between that child node's measurable weight vector and each other child node's measurable weight vector, and further normalizing the new node weights to sum to 1 by dividing all new node weights by the sum of all new node weights.

When the Strength formula is applied to score a meta-HYP with such weighting factors, the formula becomes:

$$\mathrm{Strength} = \sum_i W_i d_i \beta_i, \; W_i = \frac{w_i}{\sum_j w_j}$$

where $\beta_i$ is the score for downstream HYP i or the log-fold-change of the measurement for node i, $d_i \in \{-1, +1\}$ is a direction associated with the predicted regulation (increase or decrease) of node i in the meta-HYP, and $w_i$ is the overlap weight of node i as defined above.

In general, multiple weights associated with a downstream node in a HYP can be combined into a single weight $W_i$ by multiplying the weights together and normalizing by the sum across all nodes of the product the weights for each node. For example, to combine the overlap weights ($w_i$) and DPH weights ($w^{DPH}{}_i$) into a single weight for each node in a meta-HYP:

$$W_i = \frac{w_i w_i^{DPH}}{\Sigma_j w_j w_j^{DPH}}$$

Enabling Technologies

The techniques described herein are implemented using computer-implemented enabling technologies such as described in commonly-owned, co-pending applications U.S. Publication No. 2005/00038608, No. 2005/0165594, No. 2005/0154535, and No. 2007/0225956. These patent applications, the disclosures of which are incorporated herein by reference, describe a casual-based systems biology modeling tool and methodology. In general, this approach provides a software-implemented method for hypothesizing a biological relationship in a biological system that uses a database comprising a multiplicity of nodes representative of biological elements, and relationship descriptors describing relationships between nodes, the nodes and relationship descriptors in the database comprising a collection of biological assertions from which one or more candidate biological assertions are chosen. After selecting a target node in the database for investigation, a perturbation is specified for the target node. In response, given nodes and relationship descriptors of the database that potentially affect or are affected by the target node are traversed. In response to data generated during the traversing step, candidate biological assertions can be identified for further analysis. These biological assertions, and the nodes described therein, comprise the signature of interest for the target node (i.e., the signature's reference node).

Aspects of this disclosure may be practiced, typically in software, on one or more machines or computing devices. Generalizing, a machine or computing device (a "computing entity") typically comprises commodity hardware and software, storage (e.g., disks, disk arrays, and the like) and memory (RAM, ROM, and the like). The particular computing entities used in the system are not a limitation of the present invention. A given machine includes network interfaces and software to connect the machine to a network in the usual manner. The subject matter or features thereof may be implemented as a standalone product, or as a managed service using a set of machines, which are connected or connectable to one or more networks. More generally, the product or service is provided using a set of one or more computing-related entities (systems, machines, processes, programs, libraries, functions, or the like) that together facilitate or provide the inventive functionality described above. In a typical implementation, the service comprises a set of one or more computers. A representative machine is a network-based server running commodity (e.g. Pentium-class) hardware, an operating system (e.g., Linux, Windows, OS-X, or the like), an application runtime environment (e.g., Java, .ASP), and a set of applications or processes (e.g., AJAX technologies, Java applets or servlets, linkable libraries, native code, or the like, depending on platform), that provide the functionality of a given system or subsystem. A display may be used to provide an output. As described, the product or service (or any function thereof) may be implemented in a standalone server, or across a distributed set of machines, or in any a tablet or handheld computing device. Typically, a server or computing device connects to the publicly-routable Internet, an intranet, a private network, or any combination thereof, depending on the desired implementation environment.

According to another aspect, a computer program product comprising computer-readable instructions is provided. The computer-readable instructions, when loaded and executed on a computer system, cause the computer system to operate according to the various computational methods described above.

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a standalone machine, or across a distributed set of machines.

A computing platform in which aspects of this invention may be practiced comprises co-located hardware and software resources, or resources that are physically, logically, virtually and/or geographically distinct. Communication networks used to communicate to and from the platform may be packet-based, non-packet based, and secure or non-secure, or some combination thereof.

One or more functions of such a technology platform may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The above-described mathematical derivations are intended to be representative and non-limiting. The techniques may be used, among other ways, to quantify assessment of biological impact of active substances, to characterize biological network response, to mechanistically assess the biological impact of a complex perturbation of an in vivo system, or the like. The approach herein facilitates a unified and coherent framework for scoring biological entities ranging from individual molecular mechanisms to systems-level processes, as well as methods for computing scores for each level. As has been described, a score represents an objective assessment of a degree of activation based on the known effects of that activity, e.g., differential expression of genes, differential levels or activities of other biological molecules (e.g., proteins), or the like. The quantitative methodology described herein provides comprehensive mechanistic insights into the biological response to exposures measured by transcriptomics. One possible utility of this methodology is to provide a comparative assessment of the biological impact of different therapeutic agents in order to understand their relative effects on a range of biological processes (including both therapeutically relevant and irrelevant processes). Further, the biological impact of environment exposures of consumer products could be assessed as a novel approach for systems toxicology.

Thus, for example, one application of the above-described network scoring methodology is for the evaluation of the possible effects of exposure to environmental toxins. In such a scenario, the biological networks represent various pathways for sensing and reacting to cell stresses, such as the oxidative stress response, DNA damage response, and apoptosis signaling pathways. Transcriptomic data is collected from an experiment where cell lines or animal models are exposed to a toxin of interest, and network scores are computed from this transcriptomic data. The specific network scores are then used to assess which biological pathways are affected by the toxin. Additionally, the network scores may be compared across different toxins to evaluate and/or rank the relative effects of the toxins on different pathways. For example, toxins could be ranked from highest to lowest scores for an oxidative stress pathway to determine which toxins are potentially stronger inducers of oxidative stress. Across a range of biological networks, such an approach provides an assessment of the relative impacts of various toxins on different pathways, providing a means of comparing the toxicity profiles of toxins and estimating exposure limits of one toxin by comparing its network and subnetwork scores to those of another toxin with known exposure effects and toxicity limits.

Another example application is in the evaluation of the effects of therapeutic drugs or treatments. Appropriate experimental systems (for example, cell lines or animal models) are treated with a drug, and transcriptomic data is collected. Networks representing the target pathway (or pathways) of a drug are scored to assess the impact of a drug, and networks representing related signaling pathways are scored to examine potential off-target effects of the drug. Furthermore, networks representing various stress and toxicity pathways may be scored to assess potential toxicity effects of the drug. Finally, various doses of a single drug, or various drugs targeting the same pathway (or pathways) are compared for their effects in the target pathway(s), related pathways, and toxicity pathways to identify doses or drugs with desired effects.

These are merely representative use cases.

Having described our invention, what we now claim is set forth below.

The invention claimed is:

1. A method to determine a score for a degree of activation of an original network among a set of networks, the original network composed of causal connections among a set of nodes that represent biological entities, processes or other networks, the original network having a reference node, comprising:
    (a) constructing a listing representative of a tree graph of tree-depth 1 comprising a root node, and a set of child nodes, wherein the root node of the tree graph represents the original network, and wherein each child node represents a particular node in the original network and is connected to the root node by a signed, directed edge pointing from the root node to that child node;
    wherein a sign of the signed, directed edge from the root node to that child node is determined from the signs of one or more paths connecting the particular node in the original network to the reference node in the original network;
    wherein each child node also has a weight associated therewith, the node weight being based on the one or more paths connecting the particular node in the original network to the reference node in the original network;
    (b) scoring the tree graph based on scores assigned to the child nodes and the signs of the signed, directed edges; and
    (c) computing a new node weight for each child node by dividing the weight associated with each child node by the number of other networks in the set of networks that also contain that child node, and further normalizing the new node weights to sum to 1 by dividing all new node weights by the sum of all new node weights;
    wherein at least one of the constructing, scoring and computing steps are implemented in software executing in a hardware element.

2. A method to determine a score for a degree of activation of an original network, the original network composed of causal connections among a set of nodes that represent biological entities, processes or other networks, the original network having a reference node, comprising:
    (a) constructing a listing representative of a tree graph of tree-depth 1 comprising a root node, and a set of child nodes, wherein the root node of the tree graph represents the original network, and wherein each child node represents a particular node in the original network and is connected to the root node by a signed, directed edge pointing from the root node to that child node;
    wherein a sign of the signed, directed edge from the root node to that child node is determined from the signs of one or more paths connecting the particular node in the original network to the reference node in the original network;
    wherein each child node also has a weight associated therewith, the node weight being based on the one or more paths connecting the particular node in the original network to the reference node in the original network;
    (b) scoring the tree graph based on scores assigned to the child nodes and the signs of the signed, directed edges;
    (c) computing the cosine similarity of each pair of scored child nodes, where the cosine similarity is the cosine between vectors of the weights for each measurable used to compute each child node score;
    (d) computing a new node weight for each child node by dividing the original node weight by the sum of the cosines between that child node's measurable weight vector and each other child node's measurable weight vector, and further normalizing the new node weights to sum to 1 by dividing all new node weights by the sum of all new node weights;
    wherein at least one of the constructing, scoring and computing steps are implemented in software executing in a hardware element.

* * * * *